United States Patent [19]
Lapidus et al.

[11] Patent Number: 5,928,870
[45] Date of Patent: *Jul. 27, 1999

[54] METHODS FOR THE DETECTION OF LOSS OF HETEROZYGOSITY

[75] Inventors: Stanley N. Lapidus, Bedford, N.H.; Anthony P. Shuber, Milford, Mass.

[73] Assignee: Exact Laboratories, Inc., Maynard, Mass.

[*] Notice: This patent is subject to a terminal disclaimer.

[21] Appl. No.: 08/876,857

[22] Filed: Jun. 16, 1997

[51] Int. Cl.⁶ .................................................. C12Q 1/68
[52] U.S. Cl. .............................................. 435/6; 536/24.3
[58] Field of Search ................................. 435/6; 536/24.3

[56] References Cited

U.S. PATENT DOCUMENTS

| | | |
|---|---|---|
| 4,101,279 | 7/1978 | Aslam . |
| 4,309,782 | 1/1982 | Paulin . |
| 4,333,734 | 6/1982 | Fleisher . |
| 4,445,235 | 5/1984 | Slover et al. . |
| 4,535,058 | 8/1985 | Weinberg et al. . |
| 4,683,195 | 7/1987 | Mullis et al. . |
| 4,705,050 | 11/1987 | Markham . |
| 4,735,905 | 4/1988 | Parker . |
| 4,786,718 | 11/1988 | Weinberg et al. . |
| 4,857,300 | 8/1989 | Maksem . |
| 4,871,838 | 10/1989 | Bos et al. . |
| 4,981,783 | 1/1991 | Augenlicht . |
| 4,982,615 | 1/1991 | Sultan et al. . |
| 5,087,617 | 2/1992 | Smith . |
| 5,126,239 | 6/1992 | Livak et al. . |
| 5,137,806 | 8/1992 | LeMaistre et al. . |
| 5,149,506 | 9/1992 | Skiba et al. . |
| 5,196,167 | 3/1993 | Guadagno et al. . |
| 5,248,671 | 9/1993 | Smith . |
| 5,272,057 | 12/1993 | Smulson et al. . |
| 5,302,509 | 4/1994 | Cheeseman . |
| 5,330,892 | 7/1994 | Vogelstein et al. . |
| 5,331,973 | 7/1994 | Fiedler et al. . |
| 5,348,855 | 9/1994 | Dattagupta et al. . |
| 5,352,775 | 10/1994 | Albertsen et al. . |
| 5,362,623 | 11/1994 | Vogelstein et al. . |
| 5,369,004 | 11/1994 | Polymeropoulos et al. . |
| 5,378,602 | 1/1995 | Polymeropoulos et al. . |
| 5,380,645 | 1/1995 | Vogelstein . |
| 5,380,647 | 1/1995 | Bahar . |
| 5,382,510 | 1/1995 | Levine et al. . |
| 5,409,586 | 4/1995 | Kamahori et al. . |
| 5,458,761 | 10/1995 | Kamahori et al. . |
| 5,463,782 | 11/1995 | Carlson et al. . |
| 5,466,576 | 11/1995 | Schulz et al. . |
| 5,468,610 | 11/1995 | Polymeropoulos et al. . |
| 5,468,613 | 11/1995 | Erlich et al. . |
| 5,489,508 | 2/1996 | West et al. . |
| 5,492,808 | 2/1996 | de la Chapelle et al. . |
| 5,496,470 | 3/1996 | Lenhart . |
| 5,508,164 | 4/1996 | Kausch et al. . |
| 5,512,441 | 4/1996 | Ronal . |
| 5,514,547 | 5/1996 | Balazs et al. . |
| 5,527,676 | 6/1996 | Vogelstein et al. . |
| 5,532,108 | 7/1996 | Vogelstein . |
| 5,580,729 | 12/1996 | Vogelstein . |
| 5,709,998 | 1/1998 | Kinzler et al. . |

FOREIGN PATENT DOCUMENTS

| | | |
|---|---|---|
| A-11325/95 | 10/1994 | Australia . |
| 0 284 362 A2 | 9/1988 | European Pat. Off. . |
| 0 337 498 | 10/1989 | European Pat. Off. . |
| 0 390 323 A2 | 10/1990 | European Pat. Off. . |
| 0 390 323 A3 | 10/1990 | European Pat. Off. . |
| 0 407 789 A1 | 1/1991 | European Pat. Off. . |
| 0 407 789 B1 | 1/1991 | European Pat. Off. . |
| 0 608 004 A2 | 7/1994 | European Pat. Off. . |
| 0 259 031 B1 | 11/1994 | European Pat. Off. . |
| 0 664 339 A1 | 7/1995 | European Pat. Off. . |
| WO 92/13103 | 8/1992 | WIPO . |
| WO 93/18186 | 9/1993 | WIPO . |
| WO 93/20233 | 10/1993 | WIPO . |
| WO 94/00603 | 1/1994 | WIPO . |
| WO 94/09161 | 4/1994 | WIPO . |
| WO 94/10575 | 5/1994 | WIPO . |
| WO 94/11383 | 5/1994 | WIPO . |
| WO 95/07361 | 3/1995 | WIPO . |
| WO 95/09928 | 4/1995 | WIPO . |
| WO 95/09929 | 4/1995 | WIPO . |
| WO 95/12606 | 5/1995 | WIPO . |
| WO 95/13397 | 5/1995 | WIPO . |
| WO 95/15400 | 6/1995 | WIPO . |
| WP 95/16792 | 6/1995 | WIPO . |
| WO 95/18818 | 7/1995 | WIPO . |
| WO 95/19448 | 7/1995 | WIPO . |
| WO 95/25813 | 9/1995 | WIPO . |
| WO 95/31728 | 11/1995 | WIPO . |
| WO 96/01907 | 1/1996 | WIPO . |
| WO 96/06951 | 3/1996 | WIPO . |
| WO 96/08514 | 3/1996 | WIPO . |
| WO 96/12821 | 5/1996 | WIPO . |
| WO 96/13611 | 5/1996 | WIPO . |

OTHER PUBLICATIONS

Bos et al., Nature 327:293–297, May 1987.

Segel, "Biochemical Calculations," John Wiley & Sons, Inc. NY, 1976.

Sanger, F., S. Nicklen and A.R. Coulson (Dec. 1977) "DNA sequencing with chain-terminating inhibitors" vol. 74, No. 12 *Proc. Natl. Acad. Sci. USA* pp. 5463–5467.

Wallace R.B., et al. (1979) "Hybridization of synthetic oligodeoxyribonucleotides to $\Phi_{102}$ 174 DNA: the effect of single base pair mismatch" vol. 6, No. 11 *Nucleic Acids Research* pp. 3543–3557.

Coll P., K. Phillips, and F. C. Tenover (Oct. 1989) "Evaluation of a Rapid Method of Extracting DNA from Stool Samples for Use in Hybridization Assays" vol. 27, No. 10 *Journal of Clinical Microbiology* pp. 2245–2248.

Jessup J. M. and G. E. Gallick (Sep./Oct. 1992) "The Biology of Colorectal Carcinoma" *Current Problems in Cancer* pp. 263–328.

(List continued on next page.)

Primary Examiner—Scott W. Houtteman
Attorney, Agent, or Firm—Testa, Hurwitz & Thibeault, LLP

[57] ABSTRACT

Methods are provided for detecting loss of heterozygosity in a nucleic acid sample. These methods are particularly useful for identifying individuals with gene mutations indicative of early colorectal cancer.

25 Claims, 3 Drawing Sheets

OTHER PUBLICATIONS

Litia A., L. Liukkonen and H. Siitari (1992) "Simultaneous detection of two cystic fibrosis alleles using dual–label time–resolved fluorometry" 6 *Molecular and Cellular Probes* pp. 505–512.

Young G.P., and B.H. Demediu (1992) "The genetics, epidemiology, and early detection of gastrointestinal cancers" 4 *Current Opinion in Oncology* pp. 728–735.

Hoss M., et al. (Sep. 17, 1992) "Excrement analysis by PCR" *Scientific Correspondence* p. 199.

Sidransky, et al. (Apr. 3, 1992) "Identification of ras Oncogene Mutations in the Stool of Patients with Curable Colorectal Tumors" vol. 256 *Science* pp. 102–105.

Takeda S., S. Ichii, and Y. Nakamura (1993) "Detection of K–ras Mutation in Sputum by Mutant–Allele–Specific Amplification (MASA)" 2 *Human Mutation* pp. 112–117.

Leong P.K., et al. (1993) "Detection of MYCN Gene Amplification and Deletions of Chromosome 1p in Neuroblastoma by In Situ Hybridization Using Routine Histologic Sections" vol. 69, No. 1 *Laboratory Investigations* pp. 43–50.

Thibodeau S.N., G. Bren, D. Schaid (May 7, 1993) "Microsatellite Instability in Cancer of the Proximal Colon" vol. 260 *Science* pp. 816–819.

Naber S. P.(Dec. 1, 1994) "Molecular Pathology—Detection of Neoplasia" 331 *New England Journal of Medicine* pp. 1508–1510.

Cave H., et al. (1994) "Reliability of PCR Directly from Stool Samples: Usefulness of an Internal Standard" vol. 16, No. 5 *BioTechniques* pp. 809–810.

Caldas, C., et al (Jul. 1, 1994) "Detection of K–ras Mutations in the Stool of Patients with Pancreatic Adenocarcinoma and Pancreatic Ductal Hyperplasia" 54 *Cancer Research* pp. 3568–3573.

Charlesworth B., P. Sniegowski and W. Stephan (Sep. 15, 1994) "The evolutionary dynamics of repetitive DNA in eukaryotes" vol. 371 *Nature* pp. 215–220.

Fearon E. R.(1995) "16 Molecular Abnormalities in Colon and Rectal Cancer" *The Molecular Basis of Cancer* pp. 340–357.

Ravelingien N., J. C. Pector & T. Velu (1995) "Contribution of molecular oncology in the detection of colorectal carcinomas" 58 *Acta Gastro–Enterologica Belgica* pp. 270–273.

Duffy M.J.(1995) "Can Molecular Markers Now Be Used for Early Diagnosis of Malignancy?" 41/10*Clin. Chem.* pp. 1410–1413.

Blum H.E.(1995) "Colorectal Cancer: Future Population Screening for Early Colorectal Cancer" vol. 31A *European Journal of Cancer*, pp. 1369–1372.

Ridanpaa M., S. Anttila and K. Husgafvel–Pursiainen (1995) "Detection of Loss of Heterozygosity in the p53 Tumor Suppressor Gene Using a PCR–based Assay" 191 *Path. Res. Pract.* pp. 399–402.

Smith–Ravin J., J. England, I.C. Talbot, W. Bodmer (1995) "Detection of c–Ki–ras mutations in faecal samples from sporadic colorectal cancer patients" 36 *Gut* pp. 81–86.

Orlow I., et al. (Oct. 18, 1995) "Deletion of the p16 and p15 Genes in Human Bladder Tumors" vol. 87, No. 20 *Journal of the National Cancer Institute* pp. 1524–1529.

Hasegawa, Y., et al., (1995) "Detection of K–ras mutations in DNAs isolated from feces of patients with colorectal tumors by mutant–allele–specific amplification (MASA)" 10 *Oncogene* pp. 1441–1445.

Loktionov A. and I. K. O'Neill (1995) "Early detection of cancer–associated gene alterations in DNA isolated from rat feces during intestinal tumor induction with 1,2–dimethylhydrazine" 6 *International Journal of Oncology* pp. 437–445.

Honchel R., K. C. Halling and S. N. Thibodeau (1995) "Genomic instability in neoplasia" vol. 6 *Seminars in Cell Biology* pp. 45–52.

Deuter R., S. Pietsch, S. Hertel and O. Muller (1995) "A method for preparation of fecal DNA suitable for PCR" vol. 23, No. 18 *Nucleic Acids Research* pp. 3800–3801.

Dib C., et al. (Mar. 14, 1996) "A comprehensive genetic map of the human genome based on 5,264 microsatellites" vol. 380 *Nature* pp. 152–154.

Cunningham C. and M.G. Dunlop (1996) "Molecular genetic basis of colorectal cancer susceptibility" 83 *British Journal of Surgery* pp. 321–329.

Mao L., et al. (Feb. 2, 1996) "Molecular Detection of Primary Bladder Cancer by Microsatellite Analysis" vol. 271 *Science* pp. 659–662.

Villa E., et al. (May 1996) "Identification of Subjects at Risk for Colorectal Carcinoma Through a Test Based on K–ras Determination in the Stool" vol. 110, No. 5 *Gastroenterology* pp. 1346–1353.

Nollau P., C. Moser, G. Weinland, and C. Wagener (1996) "Detection of K–ras Mutations in Stools of Patients with Colorectal Cancer by Mutant–enriched PCR" 66 *Int. J. Cancer* pp. 332–336.

Eguchi S., N. Kohara, K. Komuta, and T. Kanematsu (Apr. 15, 1996) "Mutations of the p53 Gene in the Stool of Patients with Resectable Colorectal Cancer" vol. 77, No. 8 *Cancer Supplement* pp. 1707–1710.

Nollau P., C. Moser, and C. Wagener (May 1996) "Isolation of DNA from Stool and Bodily Fluids for PCR Amplication" vol. 20, No. 5 *BioTechniques* pp. 784–788.

Rhyu M. S. (Mar. 6, 1996) "Molecular Mechanisms Underlying Hereditary Nonpolyposis Colorectal Carcinoma" vol. 88, No. 5 *Journal of the National Cancer Institute* pp. 240–251.

Gyllensten U. B., Allen M. (1995) "Sequencing of In Vitro Amplified DNA" In *Recombinant DNA Methodology II* (Wu, ed) pp. 565–578.

Myers, R.M., "The Pulses of Subtraction", vol. 259 Science, pp. 942–943 (1993).

Jonsson et al., From Mutation mapping to phenotype cloning: vol. 92 Proc. Natl. Sci. USA, pp. 83–85 (1995).

Watson et al. "Isolation of Differentially Expressed Sequence Tags from Human Breast Cancer" Advanced in Brief XP 000576043, pp. 4598–4602.

METHODS FOR THE DETECTION OF LOSS OF HETEROZYGOSITY

FIELD OF THE INVENTION

This invention relates to methods useful for disease diagnosis by detecting loss of heterozygosity in cellular samples containing a small amount of mutated genetic material dispersed within a large amount of normal genetic material. Methods of the invention are especially useful in the detection of genetic mutations characteristic of cancer.

BACKGROUND OF THE INVENTION

Cancer is a disease characterized by genomic instability. The acquisition of genomic instability is thought to arise from a coincident disruption of genomic integrity and a loss of cell cycle control mechanisms. Generally, a disruption of genomic integrity is thought merely to increase the probability that a cell will engage in the multistep pathway leading to cancer. However, coupled with a loss of cell cycle control mechanisms, a disruption in genomic integrity may be sufficient to generate a population of genomically unstable neoplastic cells. A common genetic change characteristic of the early stages of transformation is loss of heterozygosity. Loss of heterozygosity at a number of tumor suppressor genes has been implicated in tumorigenesis. For example, loss of heterozygosity at the P53 tumor suppressor locus has been correlated with various types of cancer. Ridanpaa, et al., *Path. Res. Pract,* 191: 399–402 (1995). The loss of the apc and dcc tumor suppressor genes has also been associated with tumor development. *Blum, Europ. J. Cancer,* 31A: 1369–372 (1995).

Loss of heterozygosity is therefore a potentially useful marker for detecting the early stages of cancer. However, in the early stages of cancer only a small number of cells within a tissue have undergone transformation. Genetic changes characteristic of genomic instability theoretically can serve as markers for the early stages of, for example, colon cancer, and can be detected in DNA isolated from biopsied colonic epithelium and in some cases from transformed cells shed into fecal material. Sidransky, et al., *Science,* 256: 102–105 (1992).

Detection methods proposed in the art are time-consuming and expensive. Duffy, supra. Moreover, methods according to the art cannot be used to identify a loss of heterozygosity or microsatellite instability in small subpopulation of cells when the cells exist in a heterogeneous (i.e., clonally impure) sample. For example, in U.S. Pat. No. 5,527,676, it is stated that tissue samples in which a mutation is to be detected should be enriched for tumor cells in order to detect the loss of heterozygosity in a p53 gene.

Colorectal cancer is a common cause of death in Western society. Any tumor or precancerous polyp that develops along the length of the colon or the rectum sheds cells or DNA into the lumen of the colon. Shed cells or cellular DNA are usually incorporated onto and into stool as stool passes through the colon. In the early stages of cancer, cancerous or precancerous cells represent a very small fraction of the shed epithelial cells or DNA in stool. Current methods for detection of colorectal cancer do not focus on detecting cancerous or precancerous cells in stool. Rather, such methods typically focus on extracellular indicia of the presence of cancer, such as the presence of fecal occult blood or carcinoembryonic antigen circulating in serum.

It is thought that sporadic colorectal cancers result from mutations in oncogenes and tumor suppressor genes. Sporadic colorectal cancer is also typically associated with massive loss of genetic material. Such mutations appear to occur at a point in the etiology of the disease that is much earlier than the point at which extracellular indicia or clinical signs of cancer are observed. If detected early, colon cancer may be effectively treated by surgical removal of the cancerous tissue. Surgical removal of early-stage colon cancer is usually successful because colon cancer begins in cells of the colonic epithelium and is isolated from the general circulation until the occurrence of invasion through the epithelial lining. Thus, detection of early mutations in colorectal cells would greatly increase survival rate.

Current non-invasive methods for detection of colon cancer involve the detection of fecal occult blood and carcinoembryonic antigen. These methods often either fail to detect colorectal cancer or they detect colorectal cancer only after it has progressed to a less treatable stage. Moreover, carcinoembryonic antigen is thought not to be an effective predictor of cancer but merely an indicator of recurrent cancer.

Invasive techniques, such as endoscopy, while effective, are expensive and painful and suffer from low patient compliance. Accordingly, current colon cancer screening methods are not practical for screening large segments of the population. See, e.g., *Blum, Europ. J. Cancer,* 31A: 1369–1372 (1995).

Therefore, there is a need in the art for simple and efficient non-invasive methods for reliable large-scale screening to identify individuals with early stage colon cancer. Such methods are provided herein.

SUMMARY OF THE INVENTION

The present invention provides methods for detecting a subpopulation of genomically transformed cells or cellular debris. Such methods detect the presence in a biological sample of a clonal subpopulation of cells which have a genome different from that of the wild type, and from bacterial, parasitic, or contaminating organisms that may also be present in the sample. Practice of the invention permits, for example, detection of a trace amount of DNA derived from cancer or precancer cells in a biological sample containing a majority of "normal" DNA. A preferred use of the methods is to reliably detect in a stool sample voided by a patient the presence of a trace amount of cells and/or cellular debris containing DNA shed into the colon at the site of an asymptomatic precancerous or cancerous lesion. The invention takes advantage of several important insights which permit, for example, reliable detection of a DNA deletion at a known genomic site characteristic of a known cancer cell type. Methods of the invention are useful for the detection and diagnosis of a genetic abnormality, such as a loss of heterozygosity or, more generally, a mutation, which can be correlated with a disease, such as cancer. For purposes of the present invention, unless the context requires otherwise, a "mutation" includes modifications, rearrangements, deletions, substitutions, and additions in a portion of genomic DNA or its corresponding mRNA.

In general, the invention comprises methods for counting (i.e. enumerating) the number of molecules of a target genomic sequence present in a sample. The invention further comprises methods for comparing the number of molecules with a reference number to determine whether any difference between the two numbers is statistically significant, a statistically significant difference being indicative of loss of heterozygosity involving a genomic region comprising the target sequence. A useful reference number is the number of molecules of a reference genomic sequence. The reference genomic sequence is chosen such that the numbers of molecules of the target and reference genomic sequences are identical in normal cells which have not undergone loss of heterozygosity. When comparing the quantities of two genomic sequences in a sample, the enumerative methods are useful to identify a statistically-significant difference between the two quantities, and to correlate any difference, to a degree of defined statistical confidence, with the presence in the sample of a subpopulation of cells having an altered (e.g. Loss of heterozygosity) genomic sequence.

The invention may be divided into two general embodiments. (1) In a first general embodiment, an enumerative amount (number of copies) of a genetic region of interest in a sample (i.e. including a gene or genes, the mutation of which is known or suspected to be associated with cancer) is compared to an enumerative amount of a reference gene or gene fragment in the sample, the reference gene being a gene which is not normally associated with cancer and which normally has a low rate of mutation. A statistically-significant difference between the two enumerative amounts is indicative of genomic instability in a cellular subpopulation in the sample. (2) In a second general embodiment of the invention, an enumerative amount of a region on a maternal allele is compared to an enumerative amount of the corresponding region on a paternal allele. A statistically-significant difference between the two amounts is indicative of genomic instability.

In a preferred embodiment, enumerative detection of a nucleic acid mutation is accomplished by exposing a nucleic acid sample to first and second radionucleotides. The radionucleotides may be single nucleotides or oligonucleotide probes. The first radionucleotide is capable of hybridizing to a genetic region suspected to be mutated in cancer or precancer cells. The second radionucleotide is capable of hybridizing to a region known not to be mutated in cancer or precancer cells. After washing to remove unhybridized radionucleotides, the number of each of first and second radionucleotides is counted. A statistically-significant difference between the number of first and second radionucleotides is indicative of a mutation in a subpopulation of nucleic acids in the sample.

In preferred methods of the invention, first and second radionucleotides are isolated from other sample components by, for example, gel electrophoresis, chromatography, and mass spectrometry. Also in a preferred embodiment, either or both of the first and second radionucleotides is a chain terminator nucleotide, such as a dideoxy nucleotide. A preferred radionucleotide for use in methods of the invention is selected from the group consisting of $^{32}P$, $^{33}P$, $^{35}S$, $^{3}H$, $^{125}I$, and $^{14}C$. The number of first and second radionucleotides may be determined by counting. Methods of the invention are especially useful for the detection of massive nucleotide deletions, such as those that occur in loss of heterozygosity.

A massive loss of genetic material is detected as a reduction in the expected number in a sample of a nucleic acid fragment that is chosen to represent a genomic region suspected to be lost. For example, deletion of regions including all or part of human chromosome 18q have been associated with the development of cancer. According to the invention, a reduction in the number of cells in a sample having an intact 18q region is determined by comparing the number of a portion of the 18q region detected in the sample to the number of that region expected to occur in the sample. Similarly, a point mutation is detected by methods of the invention as a reduction in the sample of the number of wild-type nucleic acids encompassing the nucleotide suspected to be mutated. Accordingly, methods of the invention detect a mutation by detecting a reduction in the number of a nucleic acid expected to be in a sample. As described in detail below, methods of the invention are useful to detect a mutation in a heterogeneous cellular population without requiring the detection of multiple mutations.

An additional feature of the invention is that it has now been recognized that materials from cells lining the colon (e.g., a polyp or lesion) are shed onto forming stool only in a region comprising a longitudinal stripe along the length of the stool. Thus, unless the stool sample under investigation is a whole stool or comprises at least a cross-section of a stool, the sample will contain the relevant diagnostic information only by chance. The colon contains numerous bends and folds throughout its length. See, U.S. patent application Ser. No. 08/699,678 (Atty. Docket No. EXT-002), filed on Aug. 14, 1997. Epithelial cells lining the colon normally migrate from a basal position in colonic crypts, where stem cells divide by mitosis, to the top of the crypts and are then shed into the lumen. Colonic epithelial cells that line the intestinal lumen typically undergo regeneration every four to five days as a result of the rapid turnover rate through the epithelium. Accordingly, sloughed epithelial cells or their DNA are constantly being deposited in the forming stool as it passes through the lumen. As the stool proceeds toward the rectum and becomes progressively more solid (from an initial liquid state), epithelial cells are only sloughed onto the portion of the stool making contact with the portion of the lumen that formerly contained those cells in its epithelial lining. Epithelial cells of a polyp undergo the same rapid life cycle and shedding described above for normal colonic epithelial cells. Accordingly, cells shed from polyps are typically only absorbed onto the surface of the forming stool that makes contact with the polyp. However, if the stool is in a liquid state, mixing of shed polyp cells throughout the stool occurs automatically.

Accordingly, the present invention provides methods for detecting genomic changes in a subpopulation of cells in a sample of biological material. Methods of the invention are useful for the detection of changes in the nucleotide sequence of an allele in a small subpopulation of cells present in a large, heterogeneous sample of diagnostically-irrelevant biological material.

Also, in a preferred embodiment, transformed cells sought to be detected using methods according to the invention are malignant cells. Transformed cells detected according to methods of the invention may be induced transformants, transformed, for example, by a virus, by radiation, or by chemical or other carcinogenic means.

Methods of the invention may be performed on any biological sample, including tissue and body fluid samples. Particularly preferred biological samples include pus, sputum, semen, blood, saliva, cerebrospinal fluid, and urine. In an important embodiment of the invention the sample is stool which is analyzed to detect colorectal cancer or precancer. Methods of the invention may be practiced by exposing a biological sample to one or more radionucleotides in order to separately detect the number X of a first polynucleotide and the number Y of a second polynucleotide. In a preferred embodiment the radionucleotides are incorporated into oligonucleotide probes which are exposed to the sample under conditions that promote specific hybridization of the radiolabeled oligonucleotide probes with the first or second polynucleotides. In a more preferred embodiment, unlabeled oligonucleotide probes are exposed to the sample. The probes are subsequently radiolabeled using a primer extension reaction in the presence of radiolabeled nucleotides. The radiolabeled nucleotides are preferably chain terminating nucleotides, (e.g. dideoxynucleotides). The number of molecules of a polynucleotide in a sample is calculated from the measurement of the number of radioactive decay events that is specifically associated with the polynucleotide. The number of radioactive decay events is directly proportional to the number of molecules.

In a preferred embodiment the first and second radiolabeled oligonucleotides are separable from each other. For example, the first and second oligonucleotides are of different sizes and can be separated by gel electrophoresis, chromatography or mass spectrometry. In one embodiment the first and second oligonucleotides are of different lengths. In a preferred embodiment the size difference is imparted by a size marker which is specifically attached to one of the different size marks. Alternatively a different size marker is attached to each oligonucleotide. After separation, the number of radioactive decay events is measured for each oligonucleotide, and the number of molecules is calculated as described herein.

In a more preferred embodiment, the first and second oligonucleotides are of the same size but are labeled with different radioisotopes selected from, for example, $^{35}S$, $^{32}P$, $^{33}P$, $^{3}H$, $^{125}I$ and $^{14}C$. The first and second oligonucleotides are then distinguished by different characteristic emission spectra. The number of radioactive decay events is measured for each oligonucleotide without separating the two oligonucleotides from each other.

Methods of the invention are especially useful for the detection of colorectal cancer or precancerous cells in humans. For purposes of the present invention, precancerous cells are cells that have a mutation that is associated with cancer, and which renders such cells susceptible to becoming cancerous. Such methods comprise determining whether cells or nucleotide debris in a stool sample include a deletion of a polynucleotide normally present in a wild-type genome of the human or other mammal. The sample may be exposed to a plurality of first and second oligonucleotide probes under hybridization conditions, thereby to hybridize (i) first probe to copies of a first polynucleotide segment characteristic of a wild-type genomic region known or suspected not to be deleted in cells of the sample and (ii) second probe to copies of a second polynucleotide segment characteristic of the wild-type genomic region suspected of being mutated in the sample. The number of duplexes formed with each of the first and second probes is then detected and counted. The presence of a statistically-significant difference in those two numbers is indicative of the presence in the sample of a mutation that may be characteristic of colorectal cancer. Endoscopy or other visual examination procedures are then indicated.

Methods according to the invention also may be used to detect a loss of heterozygosity at an allele by determination of the amounts of maternal and paternal alleles comprising a genetic locus that includes at least one single-base polymorphism. A statistically-significant difference in the numbers of each allele is indicative of a mutation in an allelic region encompassing the single-base polymorphism. In this method, a region of an allele comprising a single-base polymorphism is identified, using, for example, a database, such as GenBank, or by other means known in the art. Probes are designed to hybridize to corresponding regions on both paternal and maternal alleles immediately 3' to the single base polymorphism. After hybridization, a mixture of at least two of the four common dideoxy nucleotides are added to the sample, each labeled with a different detectable label. A DNA polymerase is also added. Using allelic DNA adjacent the polymorphic nucleotide as a template, hybridized probe is extended by the addition of a single dideoxynucleotide that is the binding partner for the polymorphic nucleotide. After washing to remove unincorporated dideoxynucleotides, the dideoxynucleotides which have been incorporated into the probe extension are detected by determining the number of bound extended probes bearing each of the two dideoxy nucleotides in, for example, a scintillation counter. The presence of an almost equal number of two different labels mean that there is normal heterozygosity at the polymorphic nucleotide. The presence of a statistically-significant difference between the detected numbers of the two labels means that a deletion of the region encompassing the polymorphic nucleotide has occurred in one of the alleles.

Methods of the invention may be used to determine whether a patient is a candidate for follow-up invasive diagnostic or other procedures, such as endoscopy. For example, methods of the invention may be used to detect a mutation in a tumor suppressor gene or an oncogene in a subpopulation of cells in a stool sample obtained from a patient. An endoscopy procedure may then be performed on patients diagnosed with a mutation. A positive endoscopy result is then followed by polypectomy, surgery, or other treatment to remove cancerous or precancerous tissue.

Accordingly, it is an object of the invention to provide methods for detecting loss of heterozygosity in a subpopulation of cells in a cellular sample. It is a further object of the invention to provide methods for detecting a genomic change in a subpopulation of cells, wherein the genomic change is indicative of cancer. It is another object of the invention to detect a loss of heterozygosity in a genomic region associated with cancer, such as a tumor suppressor region. It is yet another object of the invention to provide methods for detecting heterozygosity and the loss thereof at single-base polymorphic nucleic acids. Finally, it is an object of the invention to provide methods for the detection of cancer, and particularly colorectal cancer by detection of cells or cellular debris indicative of cancer in a heterogeneous sample, such as a stool sample.

Further aspects of the invention will become apparent upon consideration of the following detailed description and of the drawings.

DETAILED DESCRIPTION OF THE INVENTION

Figure 1:
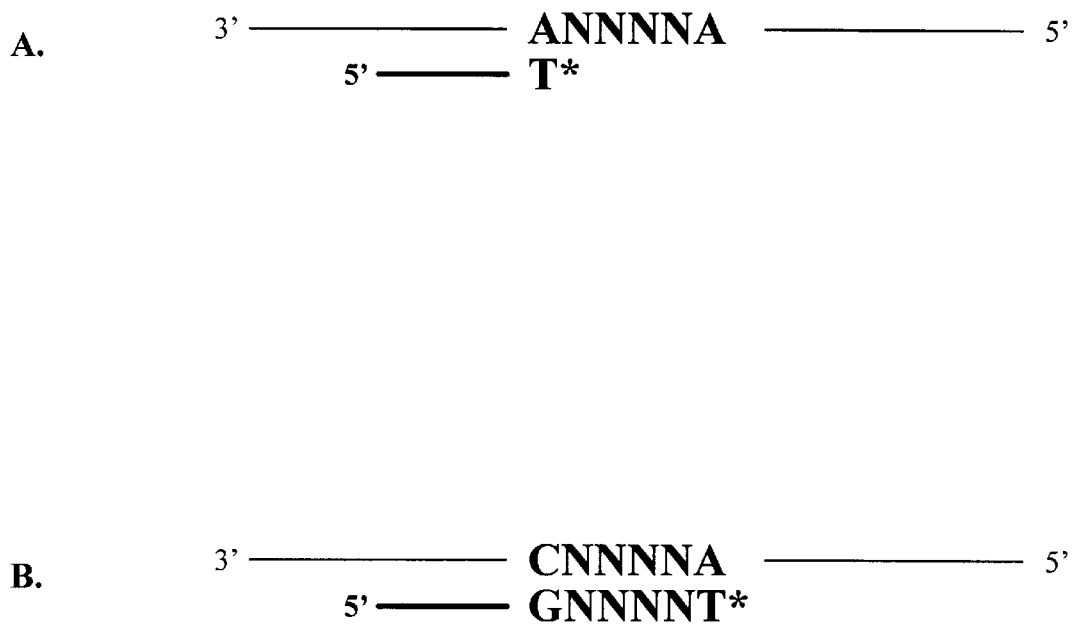
FIG. 1 depicts differential primer extension as exemplified below.

Methods according to the present invention are useful for the detection of loss of heterozygosity in a heterogeneous cellular sample in which the loss of heterozygosity occurs in only a small subpopulation of cells in the sample. Using traditional detection methods, such a subpopulation would be difficult, if not impossible, to detect especially if the deletion end points are unknown at the time of detection or a clonally-impure cellular population is used. See, e.g., U.S. Pat. No. 5,527,676 (reporting that a clonal population of cells should be used in order to detect a deletion in a p53 gene). Traditional methods for detection of mutations involved in carcinogenesis rely upon the use of a clonally-pure population of cells and such methods are best at detecting mutations that occur at known "hot spots" in oncogenes, such as k-ras. See, Sidransky, supra.

Methods of the present invention are useful for detecting loss of heterozygosity in a small number of cells in an impure cellular population because such methods do not rely upon knowing the precise deletion end-points and such methods are not affected by the presence in the sample of heterogeneous DNA. For example, in loss of heterozygosity, deletions occur over large portions of the genome and entire chromosome arms may be missing. Methods of the invention comprise counting a number of molecules of a target nucleic acid suspected of being deleted and comparing it to a reference number. In a preferred embodiment the reference number is the number of molecules of a nucleic acid suspected of not being deleted in the same sample. All that one needs to know is at least a portion of the sequence of a target nucleic acid suspected of being deleted and at least a portion of the sequence of a reference nucleic acid suspected of not being deleted. Methods of the invention, while amenable to multiple mutation detection, do not require multiple mutation detection in order to detect indicia of cancer in a heterogeneous sample.

Accordingly, methods of the present invention are useful for the detection of loss of heterozygosity in a subpopulation of cells or debris therefrom in a sample. Loss of heterozygosity generally occurs as a deletion of at least one wild-type allelic sequence in a subpopulation of cells. In the case of a tumor suppressor gene, the deletion typically takes the form of a massive deletion characteristic of loss of heterozygosity. Often, as in the case of certain forms of cancer, disease-causing deletions initially occur in a single cell which then produces a small subpopulation of mutant cells. By the time clinical manifestations of the mutation are detected, the disease may have progressed to an incurable stage. Methods of the invention allow detection of a deletion when it exists as only a small percentage of the total cells or cellular debris in a sample.

Methods of the invention comprise a comparison of the number of molecules of two nucleic acids that are expected to be present in the sample in equal numbers in normal (non-mutated) cells. In a preferred embodiment, the comparison is between (1) an amount of a genomic polynucleotide segment that is known or suspected not to be mutated in cells of the sample (the "reference") and (2) an amount of a wild-type (non-mutated) genomic polynucleotide segment suspected of being mutated in a subpopulation of cells in the sample (the "target"). A statistically-significant difference between the amounts of the two genomic polynucleotide segments indicates that a mutation has occurred.

In a preferred embodiment, the reference and target nucleic acids are alleles of the same genetic locus. Alleles are useful in methods of the invention if there is a sequence difference which distinguishes one allele from the other. In a preferred embodiment, the genetic locus is on or near a tumor suppressor gene. Loss of heterozygosity can result in loss of either allele, therefore either allele can serve as the reference allele. The important information is the presence or absence of a statistically significant difference between the number of molecules of each allele in the sample. Also in a preferred embodiment, the reference and target nucleic acids are different genetic loci, for example different genes. In a preferred embodiment, the reference nucleic acid comprises both alleles of a reference genetic locus and the target nucleic acid comprises both alleles of a target genetic locus, for example a tumor suppressor gene. Specifically, in the case of a deletion in a tumor suppressor gene, the detected amount of the reference gene is significantly greater than the detected amount of the target gene. If a target sequence is amplified, as in the case of certain oncogene mutations, the detected amount of target is greater than the detected amount of the reference gene by a statistically-significant margin.

Methods according to the art generally require the use of numerous probes, usually in the form of PCR primers and/or hybridization probes, in order to detect a deletion or a point mutation. However, because methods of the present invention involve enumerative detection of nucleotide sequences and enumerative comparisons between sequences that are known to be stable and those that are suspected of being unstable, only a few probes must be used in order to accurately assess cancer risk. In fact, a single set (pair) of probes is all that is necessary to detect a single large deletion. The risk of cancer is indicated by the presence of a mutation in a genetic region known or suspected to be involved in oncogenesis. Patients who are identified as being at risk based upon tests conducted according to methods of the invention are then directed to other, typically invasive, procedures for confirmation and/or treatment of the disease.

Enumerative sampling of a nucleotide sequence that is uniformly distributed in a biological sample typically follows a Poisson distribution. For large populations, such as the typical number of genomic polynucleotide segments in a biological sample, the Poisson distribution is similar to a normal (Gaussian) curve with a mean, N, and a standard deviation that may be approximated as the square root of N.

Statistically-significance between numbers of target and reference genes obtained from a biological sample may be determined by any appropriate method. See, e.g., Steel, et al., Principles and Procedures of Statistics, A Biometrical Approach (McGraw-Hill, 1980), the disclosure of which is incorporated by reference herein. An exemplary method is to determine, based upon a desired level of specificity (tolerance of false positives) and sensitivity (tolerance of false negatives) and within a selected level of confidence, the difference between numbers of target and reference genes that must be obtained in order to reach a chosen level of statistical significance. A threshold issue in such a determination is the minimum number, N, of genes (for each of target and reference) that must be available in a population in order to allow a determination of statistical significance. The number N will depend upon the assumption of a minimum number of mutant alleles in a sample containing mutant alleles (assumed herein to be at least 1%) and the further assumption that normal samples contain no mutant alleles. It is also assumed that a threshold differences between the numbers of reference and target genes must be at least 0.5% for a diagnosis that there is a mutation present in a subpopulation of cells in the sample. Based upon the foregoing assumptions, it is possible to determine how large N must be so that a detected difference between numbers of mutant and reference alleles of less than 0.5% is truly a negative (i.e. no mutant subpopulation in the sample) result 99.9% of the time.

Figure 2A:
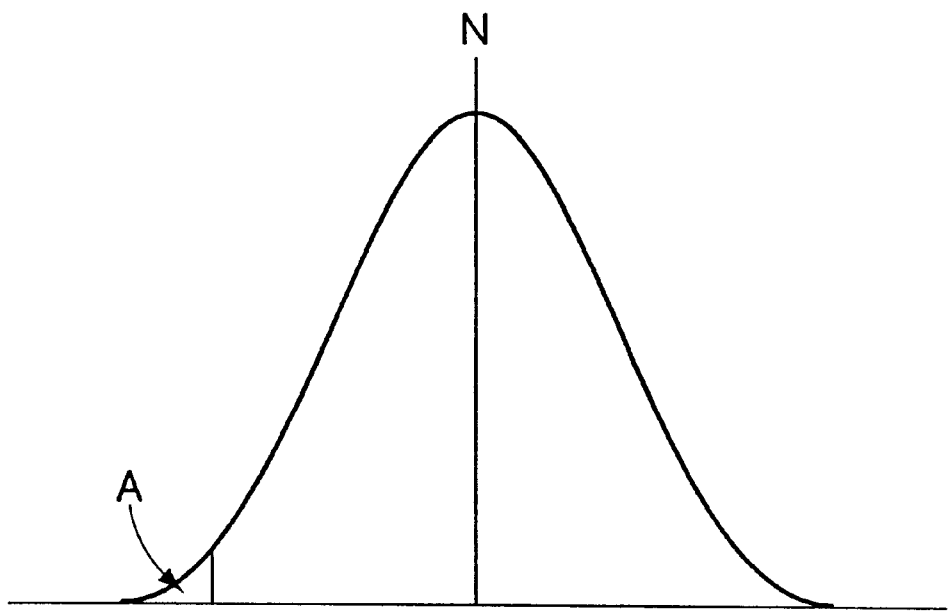
FIGS. 2A and 2B are model Gaussian distributions showing regions of low statistical probability.
Figure 2B:
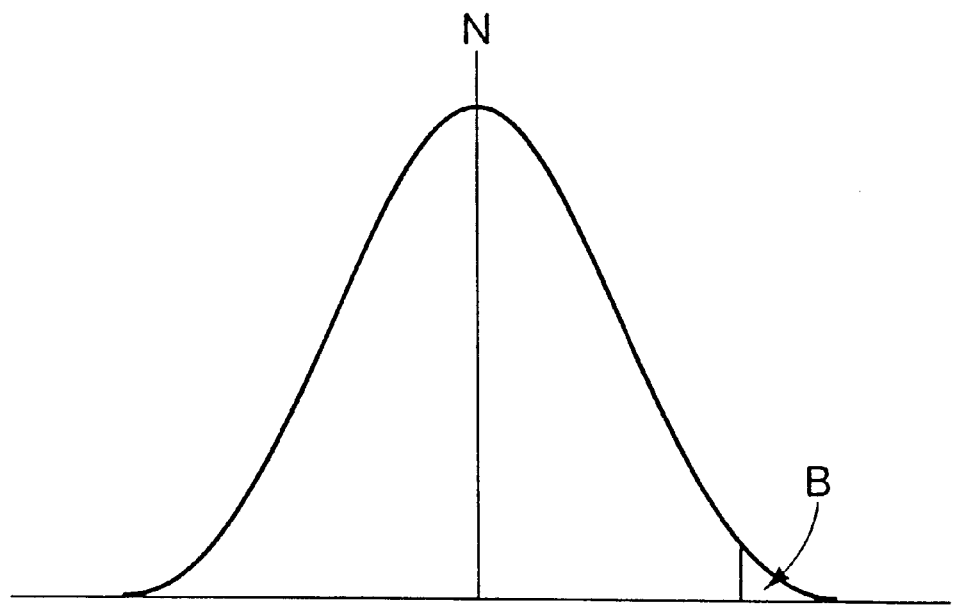

The calculation of N for specificity, then, is based upon the probability of one sample measurement being in the portion of the Gaussian distribution covering the lowest 3.16% of the population (the area marked "A" in FIG. 2A) and the probability that the other sample measurement is in the portion of the Gaussian distribution covering the highest 3.16% of the population (the area marked "B" in FIG. 2B). Since the two sample measurements are independent events, the probability of both events occurring simultaneously in a single sample is approximately 0.001 or 0.1%. Thus, 93.68% of the Gaussian distribution (100%−2×3.16%) lies between the areas marked A and B in FIG. 3. Statistical tables indicate that such area is equivalent to 3.72 standard deviations. Accordingly, 0.5% N is set equal to 3.72 sigma. Since sigma (the standard deviation) is equal to $\sqrt{N}$, the equation may be solved for N as 553,536. This means that if the lower of the two numbers representing reference and target is at least 553,536 and if the patient is truly normal, the difference between the numbers will be less than 0.5% about 99.9% of the time.

Figure 3:
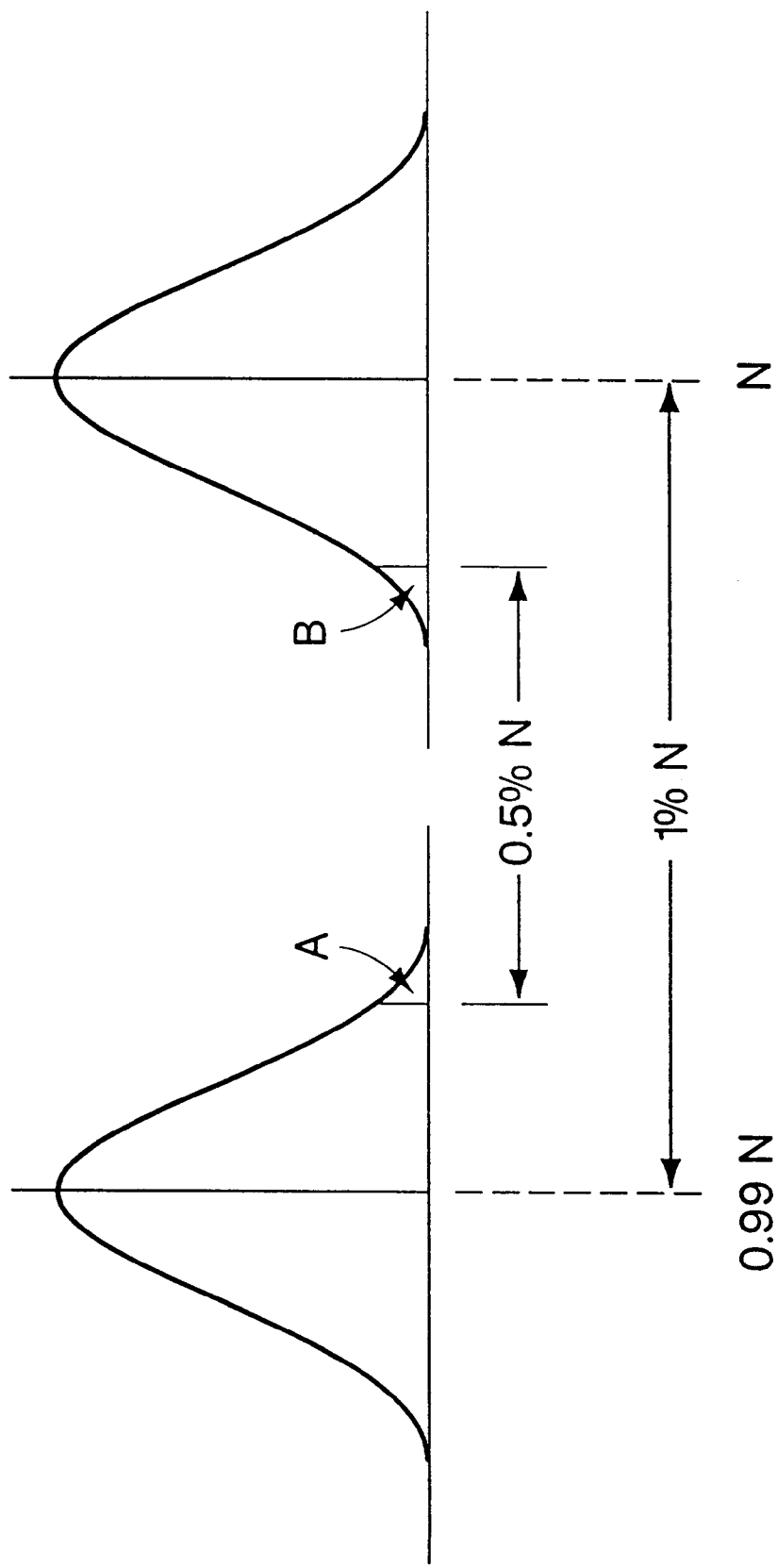
FIG. 3 is graph showing the probable values of N for a heterogeneous population of cells in which 1% of the cells are mutated.

To determine the minimum N required for 99% sensitivity a similar analysis is performed. This time, one-tailed Gaussian distribution tables show that 1.28 standard deviations (sigma) from the mean cover 90% of the Gaussian distribution. Moreover, there is a 10% (the square root of 1%) probability of one of the numbers (reference or target) being in either the area marked "A" in FIG. 3 or in the area marked "B" in FIG. 3. If the two population means are a total of 1% different and if there must be a 0.5% difference between the number of target and reference genes, then the distance from either mean to the threshold for statistical significance is equivalent to 0.25% N (See FIG. 3) for 99% sensitivity. As shown in FIG. 3, 0.25% N corresponds to about 40% of one side of the Gaussian distribution. Statistical tables reveal that 40% of the Gaussian distribution corresponds to 1.28 standard deviations from the mean. Therefore, 1.28 sigma is equal to 0.0025N, and N equals 262,144. Thus, for abnormal samples, the difference will exceed 0.5% at least 99% of the time if the lower of the two numbers is at least 262,144. Conversely, an erroneous negative diagnosis will be made only 1% of the time under these conditions.

In order to have both 99.9% specificity (avoidance of false positives) and 99% sensitivity (avoidance of false negatives), a sample with DNA derived from at least 553,536 (or roughly greater than 550,000) cells should be counted. A difference of at least 0.5% between the numbers obtained is significant at a confidence level of 99.0% for sensitivity and a difference of less than 0.5% between the numbers is significant at a confidence level of 99.9% for specificity. As noted above, other standard statistical tests may be used in order to determine statistical significance and the foregoing represents one such test.

Based upon the foregoing explanation, the skilled artisan appreciates that methods of the invention are useful to detect mutations in a subpopulation of a polynucleotides in any biological sample. For example, methods disclosed herein may be used to detect allelic loss (the loss of heterozygosity) associated with diseases such as cancer. Additionally, methods of the invention may be used to detect a deletion or a base substitution mutation causative of a metabolic error, such as complete or partial loss of enzyme activity. For purposes of exemplification, the following provides details of the use of methods according to the present invention in colon cancer detection. Inventive methods are especially useful in the early detection of a mutation (and especially a large deletion typical of loss of heterozygosity) in a tumor suppressor gene. Accordingly, while exemplified in the following manner, the invention is not so limited and the skilled artisan will appreciate its wide range of applicability upon consideration thereof.

Methods according to the invention preferably comprise comparing a number of a target polynucleotide known or suspected to be mutated to a number of a reference polynucleotide known or suspected not to be mutated. In addition to the alternative embodiments using either alleles or genetic loci as reference and target nucleic acids, the invention comprises a comparison of a microsatellite repeat region in a normal allele with the corresponding microsatellite region in an allele known or suspected to be mutated. Exemplary detection means of the invention comprise determining whether a difference exists between the number of counts of each nucleic acid being measured. The presence of a statistically-significant difference is indicative that a mutation has occurred in one of the nucleic acids being measured.

I. Preparation of a Stool Sample

A sample prepared from stool voided by a patient should comprise at least a cross-section of the voided stool. As noted above, stool is not homogenous with respect to sloughed cells. As stool passes through the colon, it absorbs sloughed cells from regions of the colonic epithelium with which it makes contacts. Thus, sloughed cells from a polyp are absorbed on only one surface of the forming stool (except near the cecum where stool is still liquid and is homogenized by Intestinal Peristalsis). Taking a representative sample of stool (i.e., at least a cross-section) and homogenizing it ensures that sloughed cells from all epithelial surfaces of the colon will be present for analysis in the processed stool sample. Stool is voided into a receptacle that is preferably small enough to be transported to a testing facility. The receptacle may be fitted to a conventional toilet such that the receptacle accepts stool voided in a conventional manner. The receptacle may comprise a mesh or a screen of sufficient size and placement such that stool is retained while urine is allowed to pass through the mesh or screen and into the toilet. The receptacle may additionally comprise means for homogenizing voided stool. Moreover, the receptacle may comprise means for introducing homogenization buffer or one or more preservatives, such as alcohol or a high salt concentration solution, in order to neutralize bacteria present in the stool sample and to inhibit degradation of DNA.

The receptacle, whether adapted to fit a toilet or simply adapted for receiving the voided stool sample, preferably has sealing means sufficient to contain the voided stool sample and any solution added thereto and to prevent the emanation of odors. The receptacle may have a support frame which is placed directly over a toilet bowl. The support frame has attached thereto an articulating cover which may be placed in a raised position, for depositing of sample or a closed position (not shown) for sealing voided stool within the receptacle. The support frame additionally has a central opening traversing from a top surface through to a bottom surface of the support frame. The bottom surface directly communicates with a top surface of the toilet. Extending from the bottom surface of the support frame and encompassing the entire circumference of the central opening is a means for capturing voided stool. The means for capturing voided stool may be fixedly attached to the support frame or may be removably attached for removal subsequent to deposition of stool.

Once obtained, the stool sample is homogenized in an appropriate buffer, such as phosphate buffered saline or a chaotropic salt solution. Homogenization means and materials for homogenization are generally known in the art. See, e.g., U.S. Pat. No. 4,101,279. Thus, particular homogenization methods may be selected by the skilled artisan. Methods for further processing and analysis of a biological sample, such as a stool sample are presented below.

II. Methods for Detection of Colon Cancer or Precancer

For exemplification, methods of the invention are used to detect a deletion or other mutation in or near the p53 tumor suppressor gene in cells obtained from a representative stool sample. The p53 gene is a good choice because the loss of heterozygosity in p53 is often associated with colorectal cancer. An mRNA sequence corresponding to the DNA coding region for p53 is reported as GenBank Accession No. M92424. The skilled artisan understands that methods described herein may be used to detect mutations in any gene and that detection of a p53 deletion is exemplary of such methods. In the detection of loss of heterozygosity, it is not necessary to target any particular gene due to the massive deletions associated with this event. Accordingly, an LOH-type deletion involving, for example, p53 may be detected by probing a region outside, but near, p53 because that region is also likely to be deleted. At least a cross-section of a voided stool sample is obtained and prepared as described immediately above. DNA or RNA may optionally be isolated from the sample according to methods known in the art. See, Smith-Ravin, et al., *Gut,* 36: 81–86 (1995), incorporated by reference herein. Methods of the invention may also comprise the step of amplifying DNA or RNA sequences using the polymerase chain reaction. However, methods of the invention may be performed on unprocessed stool.

Nucleic acids may be sheared or cut into small fragments by, for example, restriction digestion. The size of nucleic acid fragments produced is not critical, subject to the limitations described below. A target nucleic acid that is suspected of being mutated (p53 in this example) and a reference nucleic acid are chosen. The target and reference nucleic acids may be alleles on or near the p53 gene. Alternatively, the target nucleic acid comprises both alleles on or near the p53 gene and the reference nucleic acid comprises both alleles on or near a genetic locus suspected not to be deleted. Single-stranded nucleic acid fragments may be prepared using well-known methods. See, e.g., Sambrook, et al., *Molecular Cloning, A Laboratory Manual* (1989) incorporated by reference herein.

Either portions of a coding strand or its complement may be detected in methods according to the invention. In a preferred embodiment, both first and second strands of an allele are present in a sample during hybridization to an oligonucleotide probe. The sample is exposed to an excess of probe that is complementary to a portion of the first strand, under conditions to promote specific hybridization of the probe to the portion of the first strand. In a most preferred embodiment, the probe is in sufficient excess to bind all the portion of the first strand, and to prevent reannealing of the first strand to the second strand of the allele. Also in a preferred embodiment, the second strand of an allele is removed from a sample prior to hybridization to an oligonucleotide probe that is complementary to a portion of the first strand of the allele. For exemplification, detection of the coding strand of p53 and reference allele are described. Complement to both p53 and reference allele are removed by hybridization to anti-complement oligonucleotide probes (isolation probes) and subsequent removal of duplex formed thereby. Methods for removal of complement strands from a mixture of single-stranded oligonucleotides are known in the art and include techniques such as affinity chromatography. Upon converting double-stranded DNA to single-stranded DNA, sample is passed through an affinity column comprising bound isolation probe that is complementary to the sequence to be isolated away from the sample. Conventional column chromatography is appropriate for isolation of complement. An affinity column packed with sepharose or any other appropriate materials with attached complementary nucleotides may be used to isolate complement DNA in the column, while allowing DNA to be analyzed to pass through the column. See Sambrook, Supra. As an alternative, isolation beads may be used to exclude complement as discussed in detail below.

After removal of complement, the target and reference nucleic acids are exposed to radio-labeled nucleotides under conditions which promote specific association of the radio-labeled nucleotides with the target and reference nucleic acids in a sample. In order to count the number of molecules of the target and reference nucleic acids, the radionucleotides associated with the target nucleic acid must be distinguished from the radionucleotides associated with the reference nucleic acid. In addition, the radionucleotides that are specifically associated with either target or reference nucleic acid must be distinguished from radionucleotides that are not associated with either nucleic acid. The number of molecules of target nucleic acid is counted by measuring a number X of radioactive decay events (e.g. by measuring the total number of counts during a defined interval or by measuring the time it takes to obtain a predetermined number of counts) specifically associated with the target nucleic acid. The number X is used to calculate the number X1 of radionucleotides which are specifically associated with the target nucleic acid. The number X1 is used to calculate the number X2 of target nucleic acid molecules, knowing the ratio of radionucleotide molecules to target nucleic acid molecules in the assay.

According to methods of the invention, it is important to count the number of molecules in order to provide a statistical analysis of the likelihood of loss of heterozygosity. Comparison of the numbers of radioactive decays without knowing the numbers of molecules associated with the radioactive decays does not provide statistical data on the significance of any observed difference.

In a preferred embodiment, a radionucleotide is incorporated into a specific oligonucleotide prior to exposure to the sample. In a most preferred embodiment, a radiolabeled oligonucleotide is used which comprises a single radionucleotide molecule per oligonucleotide molecule. A radiolabeled oligonucleotide is designed to hybridize specifically to a target nucleic acid. In one embodiment the target nucleic acid is a specific allele of a polymorphic genetic locus, and the oligonucleotide is designed to be complementary to the allele at the site of polymorphism. One skilled in the art can perform hybridizations under conditions which promote specific hybridization of the oligonucleotide to the allele, without cross hybridizing to other alleles. Similarly, radiolabeled oligonucleotides are designed to specifically hybridize with the reference nucleic acid.

Also in a preferred embodiment, a radionucleotide is specifically incorporated into an oligonucleotide by primer extension, after exposing the oligonucleotide to the sample under conditions to promote specific hybridization of the oligonucleotide with the target nucleic acid. In a preferred embodiment the oligonucleotide is unlabeled, and the radionucleotide is a radiolabeled chain terminating nucleotide (e.g. a dideoxynucleotide). In a most preferred embodiment, the radionucleotide is the chain terminating nucleotide complementary to the nucleotide immediately 5' to the nucleotide that base pairs to the 3' nucleotide of the oligonucleotide when it is specifically hybridized to the target nucleic acid. In the embodiment where the target nucleic acid is an allele of a polymorphic genetic locus, the oligonucleotide is preferably designed such that the 3' nucleotide of the oligonucleotide base pairs with the nucleotide immediately 3' to the polymorphic residue. In a preferred embodiment, a radiolabeled terminating nucleotide that is complementary to the residue at the polymorphic site is incorporated on the 3' end of the specifically hybridized oligonucleotide by a primer extension reaction. Similarly, in a preferred embodiment, a radionucleotide is specifically associated with a reference nucleic acid by primer extension. Other methods for specifically associating a radioactive isotope with a target or reference nucleic acid (for example a radiolabeled sequence specific DNA binding protein) are also useful for the methods of the invention.

In a preferred embodiment, prior to counting the radioactive decay events, the radionucleotides specifically associated with target and reference nucleic acids are separated from the radionucleotides that are not specifically associated with either nucleic acid. Separation is performed as described herein, or using techniques known in the art. Other separation techniques are also useful for practice of the invention. Methods of the invention also comprise distinguishing the radio-label specifically associated with a target nucleic acid from the radio-label specifically associated with a reference nucleic acid. In a preferred embodiment the isotope associated with the target is different from the isotope associated with the receptor. Different isotopes useful to radio-label nucleotides include $^{35}$S, $^{32}$P, $^{33}$P, $^{125}$I, $^{3}$H, and $^{14}$C. In one embodiment, an oligonucleotide complementary to a target nucleic acid is labeled with a different isotope from an oligonucleotide complementary to a reference nucleic acid. In another embodiment, the chain terminating nucleotide associated with the target nucleic acid is different from the chain terminating nucleotide associated with the reference nucleic acid, and the two chain terminating nucleotides are labeled with different isotopes.

In a preferred embodiment, radionucleotides labeled with different isotopes are detected without separating the radionucleotide associated with the target nucleic acid from the radionucleotide associated with the reference nucleic acid. The different isotopes useful to the invention have different characteristic emission spectra. The presence of a first isotope does not prevent the measurement of radioactive decay events of a second isotope. In a more preferred embodiment, the labeled oligonucleotide associated with the target nucleic acid is the same size as the labeled oligonucleotide associated with the reference nucleic acid (the labeled oligonucleotides can be labeled prior to hybridization or by primer extension). The two differentially labeled oligonucleotides are electrophoresed on a gel, preferably a denaturing gel, and the gel is exposed to an imager that detects the radioactive decay events of both isotopes. In this embodiment the two isotopes are detected at the same position on the imager, because both oligonucleotides migrate to the same position on the gel. Detection at the same position on the imager reduces variation due to different detection efficiencies at different positions on the imager.

Also in a preferred embodiment, the radionucleotide associated with the target nucleic acid is separated from the radionucleotide associated with the reference nucleic acid prior to measuring radioactive decay events. In a preferred embodiment the separated radionucleotides are labeled with the same isotope.

Preferred separation methods comprise conferring different molecular weights to the radionucleotides specifically associated with the target and reference nucleic acids.

In a preferred embodiment, first probes comprise a "separation moiety." Such separation moiety is, for example, hapten, biotin, or digoxigenin. The separation moiety in first probes does not interfere with the first probe's ability to hybridize with template or be extended. In an alternative embodiment, the labeled ddNTPs comprise a separation moiety. In yet another alternative embodiment, both the first probes and the labeled ddNTPs comprise a separation moiety. Following the extension reaction, a high molecular weight molecule having affinity for the separation moiety (e.g., avidin, streptavidin, or anti-digoxigenin) is added to the reaction mixture under conditions which permit the high molecular weight molecule to bind to the separation moiety. The reaction components are then separated on the basis of molecular weight using techniques known in the art such as gel electrophoresis, chromatography, or mass spectroscopy. See, Ausubel et al., *Short Protocols in Molecular Biology*, 3rd ed. (John Wiley & Sons, Inc., 1995); *Wu Recombinant DNA Methodology II*, (Academic Press, 1995).

Also in a preferred embodiment the radionucleotide associated with a first allele of a polymorphic genetic locus is separated from the radionucleotide associated with a second allele of the polymorphic locus by differential primer extension, wherein the extension products of a given oligonucleotide primer are of a different length for each of the two alleles. In differential primer extension (exemplified in FIG. 1) an oligonucleotide is hybridized such that the 3' nucleotide of the oligonucleotide base pairs with the nucleotide that is immediately 5' of the polymorphic site. The extension reaction is performed in the presence of a radiolabeled terminator nucleotide complementary to the nucleotide at the polymorphic site of the first allele. The reaction also comprises non-labeled nucleotides complementary to the other 3 nucleotides. Extension of a primer hybridized to the first allele results in a product having only the terminator nucleotide incorporated (exemplified in FIG. 1A, T* is the labeled terminator nucleotide). Extension of a primer hybridized to the second allele results in a product that incorporates several non-labeled nucleotides immediately 5' to the terminator nucleotide (exemplified in FIG. 1B). The number of non-labeled nucleotides that are incorporated is determined by the position, on the template nucleic acid, of the closest 5' nucleotide complementary to the terminator nucleotide. In an alternative embodiment, differential primer extension comprises a labeled oligonucleotide and a non-labeled terminator nucleotide.

Labeled probes are exposed to sample under hybridization conditions. Such conditions are well-known in the art. See, e.g., Wallace, et al., *Nucleic Acids Res.*, 6: 3543–3557 (1979), incorporated by reference herein. First and Second oligonucleotide probes that are distinctly labeled (i.e. with different radioactive isotopes, fluorescent means, or with beads of different size) are applied to a single aliquot of sample. After exposure of the probes to sample under hybridization conditions, sample is washed to remove any unhybridized probe. Thereafter, hybridized probes are detected separately for p53 hybrids and reference allele hybrids. Standards may be used to establish background and to equilibrate results. Also, if differential fluorescent labels are used, the number of probes may be determined by counting differential fluorescent events in a sample that has been diluted sufficiently to enable detection of single fluorescent events in the sample. Duplicate samples may be analyzed in order to confirm the accuracy of results obtained.

If there is a difference between the amount of p53 detected and the amount of the reference allele detected greater than a 0.5% difference with at least 550,000 events (earlier shown to be the threshold of significance), it may be assumed that a mutation has occurred in the region involving p53 and the patient is at risk for developing or has developed colon cancer. Statistical significance may be determined by any known method. A preferred method is outlined above.

The determination of a p53 mutation allows a clinician to recommend further treatment, such as endoscopy procedures, in order to further diagnose and, if necessary, treat the patient's condition. The following examples illustrate methods of the invention that allow direct quantification of hybridization events.

What is claimed is:

1. A method for detecting the presence of a mutant nucleic acid in a sample population, comprising the steps of:
   a) introducing a first radionucleotide to a sample population suspected to contain a subpopulation of a nucleic acid mutant, wherein said first radionucleotide hybridizes to a first wild-type nucleic acid target, a subpopulation of which suspected to be mutated in the sample;
   b) introducing a second radionucleotide to the sample, wherein said second radionucleotide hybridizes to a second wild-type nucleic acid target in the sample
   c) washing said sample to remove unhybridized first and second radionucleotides;
   d) determining a number X of radioactive decay events associated with said first radionucleotide;
   e) determining a number Y of radioactive decay events associated with said second radionucleotide;
   f) determining whether a difference exists between number X and number Y, the presence of a statistically-significant difference being indicative of the presence of a mutation in said sample.

2. The method of claim 1 wherein said first radionucleotide is capable of hybridizing to a nucleic acid in the sample that is suspected to be mutated in cancer or precancer; and said second radionucleotide is capable of hybridizing to a nucleic acid in the sample that is not mutated in cancer or precancer.

3. The method of claim 1 wherein said first radionucleotide is capable of hybridizing to a portion of the maternal allele at a genetic locus; and said second radionucleotide is capable of hybridizing to a portion of the paternal allele at said locus.

4. The method of claim 1 further comprising the step of isolating said first radionucleotide specifically bound to a first target nucleic acid, and said second radionucleotide specifically bound to a second target nucleic acid.

5. The method of claim 4 wherein said isolating step is selected from the group consisting of gel electrophoresis, chromatography, and mass spectrometry.

6. The method of claim 4 wherein said number X is correlated with a number X1 of molecules of said first nucleic acid, and said number Y is correlated with a number Y1 of molecules of said second nucleic acid.

7. The method of claim 1 wherein at least one of said first and second radionucleotides is a chain terminator nucleotide.

8. The method of claim 1 wherein at least one of said first and second radionucleotides is an oligonucleotide.

9. The method of claim 1 wherein said radionucleotides are labeled with an isotope selected from the group consisting of 32P, 33P, 35S, 125I and 14C.

10. The method of claim 1 wherein each of said first and second radionucleotides are labeled with a different isotope.

11. The method of claim 10 wherein said numbers X and Y are determined by coincidence counting.

12. A method for determining the number of molecules of a nucleic acid comprising the steps of:
   a) exposing a sample to a plurality of first radionucleotides;
   b) isolating radionucleotides specifically bound to first target nucleic acid molecules;
   c) determining a number of radioactive decay events associated with the radionucleotides of step b);
   d) calculating a number of molecules of said sequence as equivalent to said number of radioactive decay events.

13. A method for detecting the presence of a mutation in a nucleic acid, comprising the steps of:
   a) exposing a sample to a plurality of a oligonucleotide;
   b) performing a primer extension reaction in the presence of a plurality of a chain terminating nucleotide, to generate extension products of said oligonucleotide;
   c) determining the size of the extension products, the presence of extension products of different sizes being indicative of the presence of a mutation.

14. The method of claim 13 wherein said oligonucleotide is capable of hybridizing to a member selected from the group consisting of a maternal allele and a paternal allele of the same genetic locus.

15. The method of claim 13 wherein said oligonucleotide is labeled.

16. The method of claim 13 wherein said terminating nucleotide is labeled.

17. The method of claims 15 or 16 wherein said label is a radioactive isotope.

18. The method of claim 13 wherein said extension reaction is performed in the presence of at least two differentially labeled chain terminating nucleotides.

19. A method for detecting loss of heterozygosity in a nucleic acid, comprising the steps of:
   a) contacting a sample with a radionucleotide;
   b) isolating a nucleic acid specifically bound to said radionucleotide;
   c) determining a number of radioactive decay events associated with said nucleic acid;
   d) comparing said number to a reference number,
   wherein a statistically significant difference between said number and said reference number is indicative of loss of heterozygosity.

20. The method of claim 1, wherein said sample comprises cellular material from a population of patients.

21. The method of claim 20, wherein said population of patients is healthy.

22. The method of claim 20, wherein said population of patients has a disease suspected to be associated with said mutant nucleic acid.

23. The method of claim 20, wherein said disease is cancer.

24. The method of claim 1, wherein said mutant nucleic acid is an allelic variant.

25. The method of claim 24, wherein said variant is a single nucleotide polymorphism.

* * * * *

UNITED STATES PATENT AND TRADEMARK OFFICE
CERTIFICATE OF CORRECTION

| | |
|---|---|
| PATENT NO. | : 5,928,870 |
| APPLICATION NO. | : 08/876857 |
| DATED | : July 27, 1999 |
| INVENTOR(S) | : Stanley Lapidus et al. |

It is certified that error appears in the above-identified patent and that said Letters Patent is hereby corrected as shown below:

Column 1, between line 2, ending "HETEROZYGOSITY", and line 4, beginning "Field of", insert the following paragraph:

--This application is a continuation-in-part of U.S. Ser. No. 08/700,583, filed on August 14, 1996, now U.S. Pat. No. 5,670,325.--

Signed and Sealed this

Thirtieth Day of December, 2008

JON W. DUDAS
*Director of the United States Patent and Trademark Office*